(12) United States Patent
Ullah et al.

(10) Patent No.: US 11,576,901 B2
(45) Date of Patent: Feb. 14, 2023

(54) METHODS FOR TREATING VIRAL INFECTION

(71) Applicants: HOWARD UNIVERSITY, Washington, DC (US); GEORGETOWN UNIVERSITY, Washington, DC (US)

(72) Inventors: Hemayet Ullah, Noth Potomac, MD (US); Sivanesan Dakshanamurthy, Herndon, VA (US)

(73) Assignees: HOWARD UNIVERSITY, Washington, DC (US); GEORGETOWN UNIVERSITY, Washington, DC (US)

( * ) Notice: Subject to any disclaimer, the term of this patent is extended or adjusted under 35 U.S.C. 154(b) by 379 days.

(21) Appl. No.: 16/088,392

(22) PCT Filed: Mar. 27, 2017

(86) PCT No.: PCT/US2017/024321
§ 371 (c)(1),
(2) Date: Sep. 25, 2018

(87) PCT Pub. No.: WO2017/165885
PCT Pub. Date: Sep. 28, 2017

(65) Prior Publication Data
US 2020/0297699 A1  Sep. 24, 2020

Related U.S. Application Data

(60) Provisional application No. 62/313,421, filed on Mar. 25, 2016, provisional application No. 62/374,413, filed on Aug. 12, 2016.

(51) Int. Cl.
*A61K 31/4196* (2006.01)
*A61K 45/06* (2006.01)

(52) U.S. Cl.
CPC .......... *A61K 31/4196* (2013.01); *A61K 45/06* (2013.01)

(58) Field of Classification Search
CPC ..... A61K 31/4196; A61K 45/06; Y02A 50/30
USPC ...................................................... 514/383
See application file for complete search history.

(56) References Cited

U.S. PATENT DOCUMENTS

2003/0143247 A1   7/2003  Robertson et al.
2005/0288347 A1  12/2005  Hodge et al.

OTHER PUBLICATIONS

Garcia et al., High-throughput Screening Using Pseudotyped Lentiviral Particles: A Strategy for the Identification of HIV-1 Inhibitors in a Cell-based Assay, Antiviral Research, vol. 81, 2009, pp. 239-247.
International Search Report for PCT/US17/024321, dated Jun. 22, 2017.

*Primary Examiner* — Taylor V Oh
(74) *Attorney, Agent, or Firm* — Sughrue Mion, PLLC

(57) ABSTRACT

A method effective in treating a viral infection involves administering a therapeutically effective amount of at least one compound capable of inhibiting expression of at least a portion of a virus genome containing an internal ribosomal entry site, or a pharmaceutically acceptable salt thereof. The compound has an azole moiety comprising a five member heterocyclic ring containing at least one nitrogen atom, a hydrophobic moiety bonded to the heterocyclic ring of the azole, and a donor/acceptor moiety bonded to the heterocyclic ring having at least one of hydrogen bond donor and a hydrogen bond acceptor.

12 Claims, 8 Drawing Sheets

METHODS FOR TREATING VIRAL INFECTION

CROSS-REFERENCE TO RELATED APPLICATIONS

This application is a U.S. national phase application filed under 35 U.S.C. § 371 of International Application No. PCT/US17/24321, filed Mar. 27, 2017, designating the United States, which claims priority from U.S. Provisional Application No. 62/374,413, filed Aug. 12, 2016, and U.S. Provisional Application No. 62/313,421, filed Mar. 25, 2016, and the complete disclosures of all the applications are hereby incorporated herein by reference in their entirety.

FIELD

A method of treating an infection of a virus containing a genome having an internal ribosome entry site is described.

BACKGROUND

Ribosomes in many ways are the factories of cells. They are the part of cells that assemble proteins which provide structural scaffolding and carry out many of the important functions necessary for cells to survive and grow. Ribosomes synthesize proteins based upon instructions received from cellular DNA. For each protein a cell needs to have manufactured at the ribosomes, an mRNA copy of the DNA detailing the primary structure of the protein to be manufactured is sent to the ribosomes.

Each of the many ribosomes within a cell contains a small subunit and a large subunit. The mRNA containing the instructions for the protein to be manufactured attaches to the small subunit. After receiving the mRNA instructions, the small subunit, holding the mRNA, attaches to the large subunit. The protein is then manufactured by the large subunit sequentially adding amino acids, the building blocks of proteins. In order for a ribosome to manufacture a protein, the small subunit and the large subunit need to join together. Accordingly, blocking the small subunit from attaching to the large subunit shuts down protein production at the ribosome.

Eukaryotic Initiation Factors (eIF) control protein production by ribosomes. Some, such as eIF-6, shut down protein production by binding to the large subunit of the ribosome. Accordingly, when cells are no longer growing or otherwise not in need of large scale protein production, ribosomes are shut down by the binding of eIF-6 to the large subunit.

After protein production has been shut down, cells may need the production of new proteins to survive. For instance, the cell might suddenly need proteins necessary to repair damage, manufacture nutrient it is suddenly deprived of, or otherwise deal with a change in its environment. When such need arises, special orders for proteins can be put in that place shut down ribosomes back to work. Special orders for protein production are indicated by a certain code in the mRNA instructions for a protein called an Internal Ribosome Entry Site (IRES). An mRNA containing an IRES code causes the eIF-6 blocking the small subunit from binding to large subunit to be removed from the large subunit. Consequently, when an IRES removes an eIF-6 the small subunit can bind to the large subunit and put the ribosome to work manufacturing the suddenly needed protein.

SUMMARY

A method of treating an infection of a virus containing a genome having an IRES is described. Viruses replicate by hijacking ribosomes and other cellular components. For the most part, viruses themselves are incapable of manufacturing proteins. Accordingly, to acquire all the proteins needed to replicate, viruses must hijack the ribosomes of the cells they infect. They do so by sending mRNA detailing the production of their viral proteins to ribosomes within the infected cell. If the ribosomes, however, have been shut down by eIF-6, then the ribosome will not manufacture the viral protein.

Some viruses, such as the HIV1 virus, get around ribosomal shutdown by containing within their genome an IRES sequence. When mRNA corresponding to this portion of the genome reaches the ribosomes of the infected cell, it has the features of a special order placed by the infected cell. As such, eIF-6 is removed and protein production at the ribosomes resumes. Accordingly, some viruses proliferate by causing mRNA for viral proteins to be delivered to the ribosomes that seem like specials orders for proteins from the infected cell.

Given that some viruses, such as the HIV1 virus, proliferate by utilizing IRES sequences to hijack ribosomes of infected cells, infections of a virus containing an IRES sequence within its genome can be treated by administering a therapeutically effective amount of a compound capable of inhibiting expression of at least a portion of a virus genome or administering a pharmaceutically acceptable salt thereof.

As the removal of eIF-6 allows a ribosome to begin production of special order mRNAs containing an IRES, inhibiting of the removal of eIF-6 would also be effective in treating infections of a virus containing an IRES sequence within it genome. Believed to be involved in the removal of eIF-6 in response to special order mRNAs containing an IRES is Receptor for Activating C Kinase I (RACK1), which is associated with the small subunit of the ribosome. It is believed that when the small subunit binds to an mRNA containing an IRES, RACK1 is phosphorylated and eIF-6 is removed from the large ribosomal subunit. With the eIF-6 removed, the small and large subunit of the ribosome can assemble and production of the protein encoded in the mRNA containing the IRES can begin.

Accordingly, administering a compound capable of inhibiting the removal of eIF-6 by RACK1 or administering a pharmaceutically acceptable salt thereof would be effective in treating infections of a virus containing an IRES sequence within its genome by inhibiting production of at least a portion of a virus genome containing an IRES sequence.

As with ribosomes, RACK1 also has a state of inactivation. When in the deactivated state, RACK1 will not remove eIF-6 from the large subunit of the ribosome. Accordingly, RACK1 may first have to be activated before the protein corresponding to the mRNA containing an IRES can be synthesized. Activation of RACK1 is believed to be controlled by phosphorylation of a tyrosine residue at or near the 248 position ($Tyr^{248}$). Phosphorylation of RACK1 may be inhibited by a molecule or other such compound that prevents access to $Tyr^{248}$. Accordingly, administering a compound capable of associating with RACK1 and blocking access to $Tyr^{248}$, or pharmaceutically acceptable salt thereof, would be effective in treating infections of a virus containing an IRES sequence within its genome by inhibiting production of at least a portion of a virus genome containing an IRES sequence.

Thus, in one of its aspects, a method of treating a viral infection comprises administering a therapeutically effective amount of a compound capable of inhibiting expression of at least a portion of the viral genome containing an internal ribosomal entry site, or a pharmaceutically acceptable salt thereof, in which the compound comprises an azole moiety comprising a five member heterocyclic ring containing at least one nitrogen atom, a hydrophobic moiety bonded to the heterocyclic ring of the azole, and a donor/acceptor moiety bonded to the heterocylic ring in which the donor/acceptor moiety comprises at least one hydrogen bond donor and a hydrogen bond acceptor.

In any of its aspects, in a present method the five member heterocyclic ring of the azole moiety comprises a nitrogen at the 1 position. In various of its aspects, the five member heterocyclic ring of the azole moiety comprises a nitrogen at the 3 position and nitrogen at the 4 position.

In any of its aspects, in a present method in the compound(s) a hydrophobic moiety can be bonded to the heterocyclic ring of the azole moiety at a first position on the ring adjacent the nitrogen comprising the hydrophilic moiety, and the donor/acceptor moiety is bonded to the heterocyclic ring of the azole moiety at a second position on the ring that is also adjacent the nitrogen comprising the hydrophilic moiety.

In any of its aspects, in a present method the compound can further comprises a hydrophilic moiety bonded to the nitrogen atom of the heterocyclic ring of the azole moiety.

In any of its aspects, in a present method the compound can have the hydrophilic moiety bonded to the nitrogen atom of the heterocyclic ring of the azole moiety, such as the nitrogen atom at the 1 position. The hydrophilic moiety can comprises an amine.

In any of its aspects, in a present method, the hydrophobic moiety can be bonded to the ring of the azole moiety at a first position on the ring adjacent the nitrogen comprising or having the hydrophilic moiety, and the donor/acceptor moiety is bonded to the ring of the azole moiety at a second position on the ring adjacent the nitrogen comprising or having the hydrophilic moiety.

In any of its aspects, in a present method, in the compound the donor/acceptor moiety can comprises an amine moiety, an amide moiety, a thione moiety, a sulfide moiety, a sulfhydryl moiety, —C(OH)CF$_3$, —CH$_2$CH(NH$_2$)COOH, —C(O, CF$_3$)COOCH$_2$CH$_3$, and —COCF$_3$.

In any of its aspects, in a present method, in the compound the donor/acceptor moiety can comprise thioether moiety.

In any of its aspects, in a present method, the donor/acceptor moiety can further comprise: an electron withdrawing group adjacent the thioether moiety; and adjacent the electron withdrawing group one of an electron donating group and a second electron withdrawing group adjacent the electron.

In any of its aspects, in a present method, the donor/acceptor moiety can further comprises: an electron withdrawing group adjacent the thioether moiety; an electron donating group adjacent the electron withdrawing group; and a stabilizing moiety.

In any of its aspects, in a present method, the donor/acceptor moiety can comprise any of —CH$_2$CONHR, —SCH$_2$COR, and —SCH$_2$R, wherein R is a hydrogen, a hydroxyl, an aryl moiety, an aryl halide moiety, an alkyl moiety, an alkyl halide moiety, a hydrazine moiety, and diphenyl ether moiety.

In any of its aspects, in a present method in the compound, the hydrophobic moiety can comprise an aryl moiety.

In any of its aspects, in a present method, in the compound, the aryl moiety as a hydrophobic moiety can be selected from the group consisting of an aromatic ether moiety, an aromatic halide moiety, and an aromatic alcohol moiety.

In any of its aspects, in a present method the compound comprises at least one compound represented by General Formula 1.

In any of its aspects, in a present method, the compound comprises at least one compound represented by any of General Formulae 1-1 through 1-20.

In any of its aspects, in a present method, the compound includes at least one compound represented by any of General Formulae 18-20.

DETAILED DESCRIPTION

Figure 1:
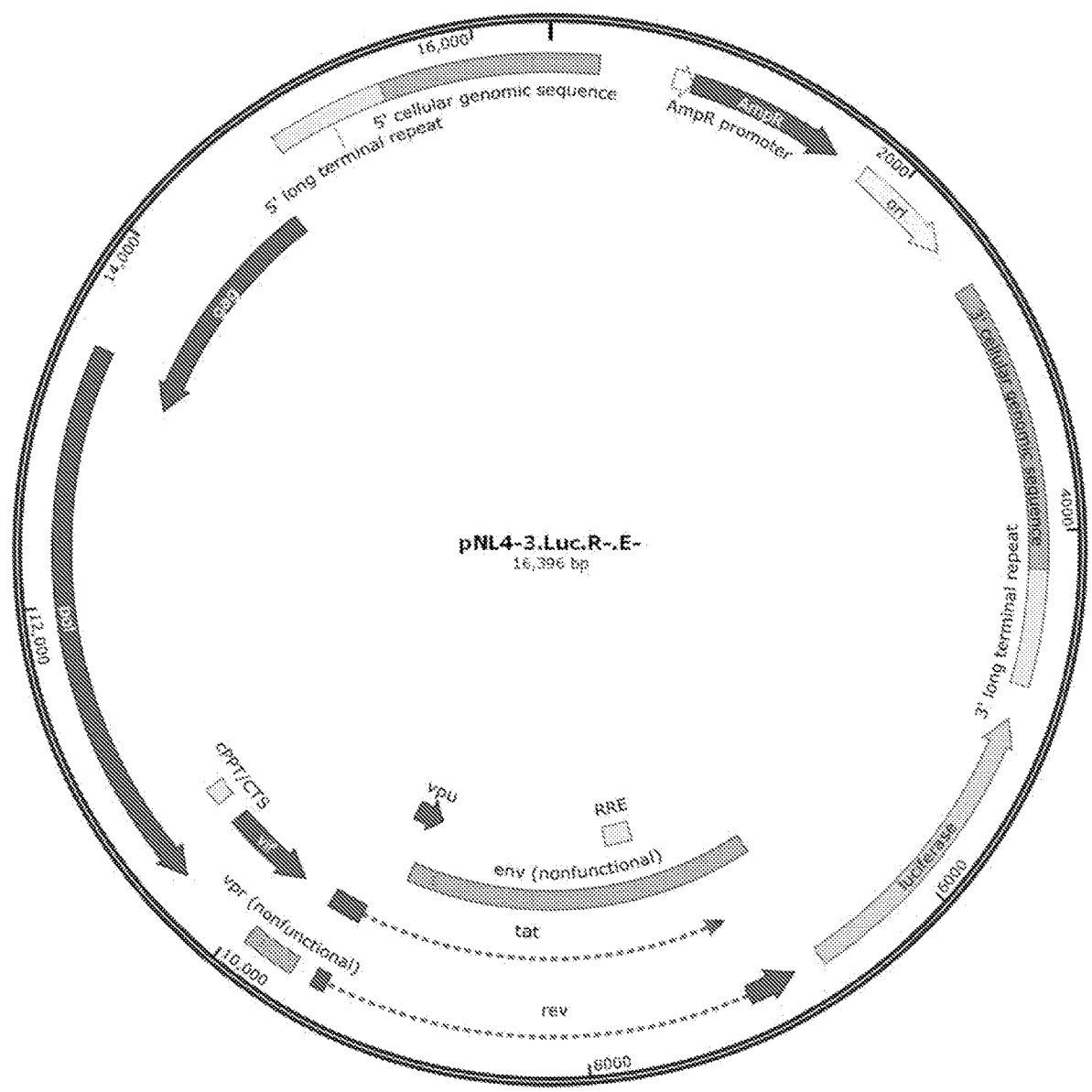
FIG. 1 illustrate a plasmid map of the pNL4-3.Luc.R-E-virus.

Infections of virus containing an IRES sequence in its genome are treated by administering a therapeutically effective amount of a compound capable of inhibiting expression of a least a portion of the viral genome or administering a pharmaceutically acceptable salt thereof, as to inhibit viral proliferation.

"Viral proliferation" refers to the expression of a viral genome, especially the complete expression. Inhibition of viral proliferation can be assessed by monitoring the expression of a specific protein within the viral genome. Accordingly, the ability of a compound, or the pharmaceutically acceptable salt of such compound, to inhibit viral proliferation can be assessed by administering the compound or its pharmaceutically acceptable salt to a cell culture and exposing the cell culture to a viral infection. After a sufficient amount of time, the culture can be examined to determine the expression of the complete viral genome by assessing the amount of at least one protein within the viral genome. If the amount of at least one protein within the viral genome is diminished compared to that within an identical infected cell culture not treated with the compound or its salt, then the compound is capable of inhibiting expression of at least a portion of the viral genome. Inhibiting proliferation of the virus infecting the cell culture comprises administering the compound, or its pharmaceutically acceptable salt to the culture in an amount effective for inhibiting expression of at least a portion of the viral genome.

The portion of the genome experiencing inhibited expression can include proteins encoded within an IRES reading frame. Alternatively or in combination, the portion the genome experiencing inhibited expression can include proteins that are not encoded within an IRES reading frame.

A "reading frame" is a portion of an mRNA molecule encoding a protein. An mRNA may have one or more reading frames. The inclusion of multiple reading frames within an mRNA allows one mRNA to include instructions for the synthesis of multiple proteins by ribosomes.

An IRES reading frame is a reading frame expressed as the result of an IRES.

The expression of protein encoded within an IRES reading frame may be necessary for viral proliferation or for the expression of other proteins necessary for viral proliferation. For instance, a virus may activate shut down ribosomes with an mRNA containing a special order IRES to produce a first viral protein, encoded within an IRES reading frame. The resulting special order viral protein may facilitate proliferation by shutting down defense mechanisms of the infected cell. In combination or the alternative, the special order viral protein may directly or indirectly activate other shut down ribosomes. In some instance the special order viral protein may be incorporated into replicated viruses. It is also possible that the special order viral protein may facilitate viral proliferation by other means. Regardless of the manner in which the special order viral protein encoded within an IRES reading frame facilitates viral proliferation, inhibiting its expression may be effective in treating infections of a virus containing an IRES sequence within its genome by inhibiting viral proliferation. Accordingly, treating a viral infection can be accomplished by administering a therapeutically effective amount of a compound or administering a pharmaceutically acceptable salt thereof capable of inhibiting expression of at least a portion of a virus genome containing an IRES sequence.

Inhibiting expression of at least a portion of the virus genome containing an IRES sequence can be accomplished by administering a compound capable of inhibiting expression of a viral protein encoded within an IRES reading frame, or a pharmaceutically acceptable salt thereof. Accordingly, by preference, in its various aspects, a present method includes administration of at least one compound described herein that has been or is assessed as inhibiting the expression of at least a portion of the virus genome containing an IRES sequence, hereinafter referred to as an assessed compound.

Compounds capable of inhibiting expression of a viral protein encoded within an IRES reading frame comprise an azole moiety comprising a five member heterocyclic ring containing at least one nitrogen atom, a first group bonded to the heterocyclic ring of the azole moiety ($G_1$), and a second group bonded to the heterocyclic ring of the azole moiety ($G_2$), as represented by General Formula 1 below.

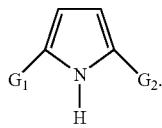

General Formula 1

Compounds in accordance with any general formulae including General Formula 1 may associate with RACK1 near $Tyr^{248}$, as to inhibit the ability of kinases, or other molecules having a similar function, from phosphorylating $Tyr^{248}$. Inhibiting the phosphorylation of $Tyr^{248}$, compounds in accordance with General Formula 1 may inhibit the removal of eIF-6 from the large ribosomal subunit, thereby inhibiting the small and large ribosomal subunits from joining together to form the ribosomal complex. Accordingly, compounds in accordance with General Formula 1 can inhibit production of a viral protein encoded within an IRES reading frame by inhibiting the ability of mRNA derived from a viral genome containing an IRES sequence from activating ribosomal protein production, and thus inhibit viral proliferation. In any aspect of a present method, the compound administered is capable of inhibiting expression of at least a portion of a virus genome containing an internal ribosomal entry site. Accordingly, embodiments include a method of treating a viral infection comprising administering a therapeutically effective amount of at least one such compound, in accordance with any of the general formula including General Formula 1, or a pharmaceutically acceptable salt thereof.

The amount of inhibition provided by a compound(s) in accordance with any of the general formulae including General Formula 1 can be improved by increasing the strength of its association with RACK1. It is important to remember that molecules, such as compounds in accordance with General Formula 1, are in a state of equilibrium between their associated and free states. Accordingly, a portion of the compounds in accordance with General Formula 1 within an infected cell will be associated with RACK1. Another portion of the compounds within the cell will not be associated with RACK1. Furthermore, any individual compound in accordance with General Formula 1 may disassociate from RACK1 returning to its free state. As a consequence of the equilibrium between free and associated compounds and the ability of associated compounds to return to their free states, a portion or the RACK1 proteins within an infected call may be left vulnerable to phosphorylation of $Tyr^{248}$. Viruses containing an IRES sequence within their genome would be free to exploit these vulnerable RACK1 proteins to hijack ribosomes and proliferate, though such proliferation would likely be diminished.

Increasing the strength of the association between RACK1 and compounds in accordance with any general formulae including General Formula 1 can limit the amount of RACK1 proteins vulnerable to phosphorylation of $Tyr^{248}$ or otherwise decrease proliferation of viruses containing an IRES sequence within their genome.

The association between RACK1 and compounds in accordance General Formula 1 may be increased by providing elements capable of maintaining hydrophobic interactions with $Tyr^{248}$ and/or amino acid residues at or near positions 204, 263 and/or 249 of RACK1. These residues may include a phenylalanine at or near position 204 ($Phe^{204}$), a leucine at or near position 263 ($Leu^{263}$) and/or a tryptophan at or near position 249 ($Trp^{249}$). Elements capable of maintaining a hydrophobic interaction with any of $Tyr^{248}$, $Phe^{204}$, $Leu^{263}$ and $Trp^{249}$ may include hydrophobic moieties at $G_1$. Accordingly, embodiments include a method comprising administering a therapeutically effective amount of a compound in accordance with General Formula 1 comprising a hydrophobic moiety at $G_1$, or a pharmaceutically acceptable salt of such a compound.

The hydrophobic moiety at $G_1$ can comprise an aryl moiety. Exemplary aryl moieties include, but are not limited to, an aromatic ether moiety, an aromatic halide moiety, and, for instance, an aromatic alcohol moiety.

The hydrophobic moiety at $G_1$, when aryl, is such as to provide derivatives of General Formula 1 in accordance with other general formulae including General Formula 1-1, where Ar is an aryl moiety, which includes but not limited to aryl moieties such as phenyl, naphthyl, thienyl and/or indolyl moieties,

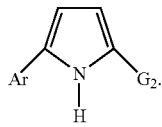

General Formula 1-1

Accordingly, embodiments include a method comprising administering a therapeutically effective amount of a compound in accordance with General Formula 1-1, or a pharmaceutically acceptable salt thereof.

The aryl moieties of any general formulae including General Formula 1-1 may be substituted as to provide aromatic ether moieties, aromatic halide moieties and/or aromatic alcohol moieties. Accordingly, substituents of the aryl moieties of General Formula 1-1 include a halogen (bromo, chloro, fluoro etc.), hydroxyl, a $C_1$ to $C_{10}$ alkyl, particularly a $C_1$ to $C_6$ alkyl, a $C_1$ to $C_{10}$ alkyl halide, a $C_1$ to $C_{10}$ alkyloxy, particularly a $C_1$ to $C_6$ alkyloxy, and/or a lower halo-alkyloxy. A $C_1$-$C_{10}$ alkyl includes methyl, ethyl, propyl, butyl, pentyl, hexyl, heptyl, octyl, nonyl, decyl. Lower halo-alkoxy includes nono-halomethoxy, difluoromethoxy, trifluoromethoxy, dicloromethoxy, trichloromethoxy, 2,2,-trichloroethoxy, dibromomethoxy, and tribromomethoxy by way of examples. Any of the forgoing substituents may be used alone or in combination. Additionally, the aryl moieties of compounds in accordance with General Formula 1-1 may include multiple instances of any of the foregoing substituents.

The association between RACK1 and a compound in accordance with General Formula 1, including derivatives in accordance with any general formulae including General Formula 1-1, may also be increased, such as, by providing elements capable of hydrogen bonding with a serine or other such amino acid residue at or near position 244 ($Ser^{244}$). In combination or as an alternative, the association between a compound in accordance with General Formula 1, including derivatives in accordance with General Formula 1-1, and RACK1 may be increased by providing elements capable of hydrogen bonding with a tryptophan or other such amino acid residue at or near position 249 ($Trp^{249}$). Such elements include, by way of example, a hydrophilic moiety attached to the nitrogen atom of the heterocyclic ring of the azole moiety, as to provide derivatives of General Formula 1 in accordance with General Formulae 1-2, and 1-3, where X is a hydrophilic moiety. Accordingly, embodiments include a method comprising administering a therapeutically effective amount of at least one compound in accordance with General Formulae 1-2 and/or 1-3, or a pharmaceutically acceptable salt thereof.

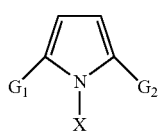

General Formula 1-2

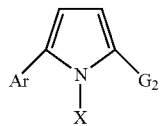

General Formula 1-3

The aryl moieties of General Formula 1-3 can include any of those specified above with regards to General Formula 1-1. Derivatives of General Formula 1 in accordance with General Formulae 1-2 and/or 1-3, include those having a hydrophilic moiety comprising an amine to provide derivatives in accordance with any of General Formulae 1-4 and/or 1-5, where X is 1 or 2. Accordingly, some embodiments comprise administering a therapeutically effective amount of at least one compound in accordance with General Formulae 1-4 and/or 1-5, or a pharmaceutically acceptable salt thereof:

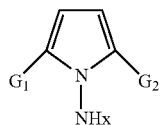

General Formula 1-4

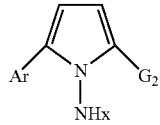

General Formula 1-5

The aryl moieties of General Formula 1-5 include any of those described herein with regards to General Formulae 1-1 and 1-3.

The association between RACK1 and compounds in accordance with General Formula 1, may also be increased, such as by providing a moiety at $G_2$ capable of hydrogen bonding with $Ser^{244}$ or the oxygen of the amide bond of $TRP^{249}$. Accordingly, embodiments include a method comprising administering a therapeutically effective amount of at least one compound in accordance with General Formula 1, including derivatives in accordance with any of General Formulae 1-1, 1-2, 1-3, 1-4, and/or 1-5, where $G_2$ comprises a donor/acceptor moiety having a hydrogen bond donor and/or a hydrogen bond acceptor, or a pharmaceutically acceptable salt of such a compound. Some embodiments thus include a method comprising administering a therapeutically effective amount of at least one compound in accordance with General Formula 1, including derivative in accordance with any of General Formulae 1-1, 1-2, 1-3, 1-4, and/or 1-5, comprising a hydrophobic moiety at $G_1$ and at $G_2$ a donor/acceptor moiety having a hydrogen bond donor and/or a hydrogen bond acceptor.

When such a compound is in accordance with any general formulae including General Formulae 1-2 and/or 1-4, the compound can comprise a hydrophilic moiety bonded to a nitrogen atom of the heterocyclic ring of the azole moiety, a hydrophobic moiety bonded to the heterocyclic ring of the azole moiety at a first position adjacent the nitrogen to which the hydrophilic moiety is bonded, and a donor/acceptor moiety having a hydrogen bond donor and/or a hydrogen bond acceptor bonded to the heterocyclic ring of the azole moiety at a second position adjacent the nitrogen to which the hydrophilic moiety is bonded. Accordingly, embodiments include a method comprising administering a therapeutic effective amount of at least one compound comprising an azole moiety, a hydrophilic moiety bonded to a nitrogen atom of the heterocyclic ring of the azole moiety, a hydrophobic moiety bonded to the heterocyclic ring of the azole moiety at a first position adjacent the nitrogen to which the hydrophilic moiety is bonded, and a donor/acceptor moiety having a hydrogen bond donor and/or a hydrogen bond acceptor bonded to the heterocyclic ring of the azole moiety at a second position adjacent the nitrogen to which the hydrophilic moiety is bonded, or pharmaceutically acceptable salt thereof.

The donor/acceptor moiety at $G_2$ in compounds in accordance with General Formula 1, including derivatives in accordance with General Formulae 1-1, 1-2, 1-3, 1-4, and/or 1-5, includes, but is not limited to, amine moieties, amide moieties, thione moieties, sulfide moieties, sulfhydryl moieties, carboxyl moieties, ketone moieties, and oxide moieties. The donor/acceptor moiety at $G_2$ can comprise any of the foregoing moieties in combination with an alkyl moiety and/or and a halide moiety. Accordingly, embodiments of a method comprise administering a therapeutic effective amount of at least one compound in accordance with General Formula 1, including derivatives in accordance with any of General Formulae 1-1, 1-2, 1-3, 1-4, 1-5, having at $G_2$ a donor/acceptor moiety which can comprise amine moieties, amide moieties, thione moieties, sulfide moieties, sulfhydryl moieties, carboxyl moieties, ketone moieties, and oxide moieties, or a pharmaceutically acceptable salt of such a compound. In some embodiments, the donor/acceptor moiety at $G_2$ can comprise any of the foregoing moieties in combination with an alkyl moiety and/or and a halide moiety.

Donor/acceptor moieties that may be used at $G_2$ in compounds in accordance with General Formula 1, including derivatives in accordance with any of the other general formulae including General Formulae 1-1, 1-2, 1-3, 1-4, and/or 1-5, include, but are not limited to, moieties in accordance with General Formulae G2-A1, G2-A2, G2-A3 and/or G2-A4:

C(OH)CF$_3$ (G2-A1),

CH$_2$CH(NH$_2$)COOH (G2-A2),

C(O,CF$_3$)COOCH$_2$CH$_3$ (G2-A3), and

COCF$_3$ (G2-A4).

These formulae are not exhaustive. For example, another suitable electron withdrawing group, by way of example can be used instead of a —CF$_3$ moiety. A —CF$_3$ moiety is representative of $C_1$-$C_6$ halo-alkyl, such as $C_1$-$C_6$ fluoroalkyl as an example, including those halo-alkyls described elsewhere herein. The term halo-alkyl includes an alkyl having more than one halogen atom. A —CH$_2$—CH$_3$ moiety is representative of $C_1$-$C_6$-alkyl, such as methyl, ethyl, propyl, butyl, pentyl, and hexyl by way of examples.

Accordingly, embodiments include a method comprising administering a therapeutic effective amount of at least one compound in accordance with General Formula 1, including derivatives in accordance with any of the other general formulae of the at least one compound, such as General Formulae 1-1, 1-2, 1-3, 1-4, and/or 1-5, having at $G_2$ a donor/acceptor moiety in accordance with any of General Formula G2-A1, G2-A2, G2-A3 and/or G2-A4, or a pharmaceutically acceptable salt thereof.

If the donor/acceptor moiety at $G_2$ in compounds in accordance with General Formula 1, including derivatives in accordance with General Formulae 1-1, 1-2, 1-3, 1-4, and/or 1-5, is a sulfide moiety then it may be advantageous to increase the strength the hydrogen bonds between the sulfur of the sulfide moiety and Ser$^{244}$ and/or the oxygen of the amide bond of Trp$^{249}$ by including within $G_2$ an electron withdrawing moiety and/or an electron donating moiety, such as but not limited to, an amide moiety and/or a ketone moiety. Though not wishing to be bound by theory, the electron withdrawing group adjacent to the thioether moiety incorporating the sulfide moiety may help to facilitate the development of a partial positive charge on the sulfur when the oxygen of the amide bond of Trp$^{249}$ approaches. As a result, a hydrogen bond interaction may develop between the sulfur and the oxygen. The resulting hydrogen bond interaction may increase the partial positive charge on the sulfur. The increased partial positive charge may cause the carbon of the thioether moiety adjacent the electron withdrawing group to become more electron withdrawing. This may in turn place an unfavorable positive charge on the electron withdrawing group destabilizing the hydrogen bond interaction. The positive charge on the electron withdrawing group may, however, be stabilized by an electron withdrawing group sufficiently close to and/or adjacent the electron withdrawing group. Alternatively or in combination, a positive charge on the electron withdrawing group may be lessen and/or alleviated by electron donating group sufficiently close to and/or adjacent the electron withdrawing group. Still not wishing to be bound by theory, the stabilized hydrogen bond interaction may facilitate a second hydrogen bond interaction between the oxygen of the hydroxyl of Ser$^{244}$ and the sulfur of the thioester moiety. As such, $G_2$ in compounds in accordance with General Formula 1, including derivatives in accordance with other general formulae including General Formulae 1-1, 1-2, 1-3, 1-4, and/or 1-5, can comprise a donor/acceptor moiety in accordance with any of General Formula G2-S1, G2-S2 and/or G2-S3:

—SCH$_2$CONHR (G2-S1),

—SCH$_2$COR (G2-S2), and

—SCH$_2$R (G2-S3).

In each of General Formulae G2-S1, G2-S2 and G2-S3, R can be a hydrogen, a hydroxyl, an aryl moiety, an aryl halide moiety, a hydrazine moiety and/or a diphenyl ether moiety.

To increase the strength of hydrogen bonds between the sulfur of a sulfide moiety at $G_2$ and Ser$^{244}$ and/or the oxygen of the amide bond of Trp$^{249}$, the use of moderate or weak electron withdrawing group in isolation may not sufficiently strengthen the hydrogen bonds. Use, however, of a moderate or weak electron withdrawing group in combination with a stabilizing moiety, such as an aromatic moiety and/or aryl halide moiety, may increase the strength of hydrogen bonds between a sulfur and Ser$^{244}$ and/or the oxygen of the amide bond of Trp$^{249}$. Likewise, use of a moderate or weak electron withdrawing group in combination with an electron donating moiety may also increase the strength of hydrogen bonds between a sulfur and Ser$^{244}$ and/or the oxygen of the amide bond of Trp$^{249}$. As such, as described above, in each of General Formulae G2-S1, G2-S2 and G2-S3, R may be a hydrogen, a hydroxyl, an aryl moiety, an aryl halide moiety, a hydrazine moiety and/or a diphenyl ether moiety. Accordingly, embodiments include a method comprising administering a therapeutic effective amount of a compound in accordance with General Formula 1, including derivatives in accordance with any of General Formulae 1-1, 1-2, 1-3, 1-4, and/or 1-5, having at $G_2$ a donor/acceptor moiety in accordance with any of General Formulae G2-S1, G2-S2 and/or G2-S3, or a pharmaceutically acceptable salt thereof.

The association between RACK1 and a compound in accordance with General Formula 1, including derivatives in accordance with any of the other general formulae including General Formulae 1-1, 1-2, 1-3, 1-4, and/or 1-5, may also be increased by hydrogen bond acceptor sites within the heterocyclic ring of the azole moiety. Hydrogen bond acceptors sites can be provided within the heterocyclic ring of the azole moiety by including a nitrogen at positions 3 and/or 4 of the ring. Accordingly, some embodiments can comprise administering a therapeutically effective amount of at least one compound in accordance with any of General Formulae 1-6, 1-7, 1-8, 1-9, 1-10, 1-11, 1-12, 1-13, 1-14, 1-15, 1-16 and/or 1-17, or a pharmaceutically acceptable salt thereof.

General Formula 1-6

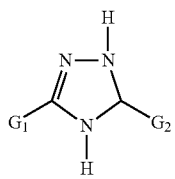

General Formula 1-7

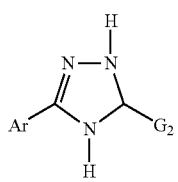

General Formula 1-8

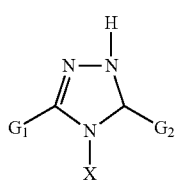

General Formula 1-9

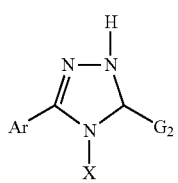

General Formula 1-10

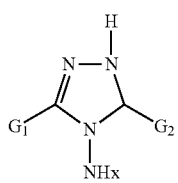

General Formula 1-11

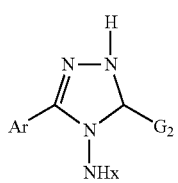

General Formula 1-12

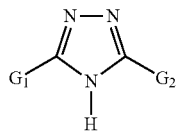

General Formula 1-13

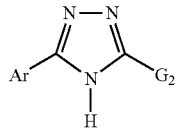

General Formula 1-14

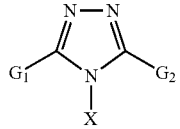

General Formula 1-15

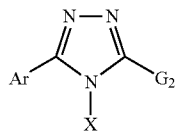

General Formula 1-16

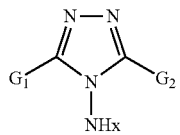

General Formula 1-17

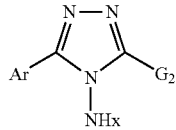

In General Formulae 1-8, 1-9, 1-14, and 1-15 X is a hydrophilic moiety.

In General Formulae 1-10, 1-11, 1-16, 1-17, x is 1 or 2. When x is 2, the substituent is —$NH_2$.

The aryl moieties in in a compound represented by General Formulae 1-17, 1-9, 1-11, 1-13, 1-15 and 1-17, include any of those specified above with regards to General Formulae 1-1 and 1-3.

In a compound represented by any of General Formulae 1-6 through 1-17, nitrogen atoms at positions 3 and/or 4 of the azole moiety may provide it electrons strengthening stacking interactions of the azole moiety.

In any compound represented by General Formulae 1-6 through 1-17, $G_2$ can comprise a hydrogen bond donor/acceptor moiety including, but not limited to, amine moieties, amide moieties, thione moieties, sulfide moieties, sulfhydryl moieties, and alkyl moieties comprising any of an amine moiety, a carboxyl moiety, a ketone moiety, an oxide moiety, and a halide moiety. Accordingly, embodiments include methods comprising comprise administering a therapeutic effective amount of at least one compound in accordance with General Formula 1, including derivatives in accordance with any of General Formulae 1-6 through 17, having at $G_2$ a donor/acceptor moiety comprising at least one of an amine moiety, an amide moiety, a thione moiety, a sulfide moiety, a sulfhydryl moiety, and an alkyl moiety that may optionally be substituted with any of a amine moiety, a carboxyl moiety, a ketone moiety, an oxide moiety, and a halide moiety, or a pharmaceutically acceptable salt of such a compound.

Alkyl moieties that may be used at $G_2$ in any compound in accordance with any of general formulae including General Formulae 1-6 through 1-17, include, but are not limited to, the alkyl moieties described with reference to General Formulae G2-A1, G2-A2, G2-A3 and G2-A4 by way of example. Accordingly, some embodiments of a method comprise administering a therapeutic effective amount of at least one compound represented by any of General Formulae 1-6 through 1-17, having at $G_2$ a donor/acceptor moiety in accordance with General Formula G2-A1, G2-A2, G2-A3 and/or G2-A4, or a pharmaceutically acceptable salt thereof.

If the donor/acceptor moiety at $G_2$ in a compound in accordance with any general formulae including General Formulae 1-6 through 1-17, is a sulfide moiety then it may be advantageous to increase the strength the hydrogen bonds between the sulfur of the sulfide and $Ser^{244}$ and/or the oxygen of the amide bond of $Trp^{249}$, such as by including within $G_2$ an electron withdrawing moiety and/or an electron donating moiety, such as but not limited to, an amide moiety and/or a ketone moiety. As such, $G_2$ in compounds in accordance with any of General Formulae 1-6 through 1-17, may comprise a donor/acceptor moiety in accordance with General Formula G2-S1, G2-S2 and/or G2-S3. Accordingly, some embodiments of a method comprise administering a therapeutic effective amount of at least one compound represented by any of General Formulae 1-6 through 1-17, having at $G_2$ a donor/acceptor moiety in accordance with any of General Formula G2-S1, G2-S2 and/or G2-S3, or a pharmaceutically acceptable salt thereof.

A compound in which the azole moiety comprises a heterocyclic group containing more than one nitrogen atom, includes a derivative of General Formula 1, such as a compound represented by General Formula 1-18:

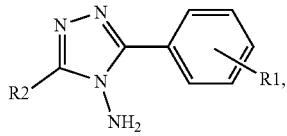

wherein $R_1$ represents a halogen, halogen-substituted lower alkyl, halogen-substituted lower alkoxy, or halogen-substituted lower alkenyl. In one of its preferred aspects, $R_2$ represents —SH. Halogen includes fluoro, bromo or chloro by way of example. Halogen-substituted lower alkyl is represented by halogen-substituted $C_1$-$C_6$ alkyl, such as difluoromethyl, trifluoromethyl, $CF_2HCH_2$— or $CF_3CH_2$— or halogen-substituted $C_6$ alkyl way of examples. Halogen-substituted lower alkoxy is represented by halogen-substituted $C_1$-$C_6$ alkoxy, such as halo-methoxy (e.g., fluoromethoxy), di-halo-methoxy (e.g., difluoromethoxy), tri-halo-methoxy (e.g., $F_3CO$—), $FCH_2$—$CH_2$— by way of examples. It will be appreciated, however, that with halogen-substituted lower alkyl and halogen-substituted lower alkoxy that the halogen is not limited to fluoro, and can be, for instance, chloro or bromo. $R_1$ can be an ortho, meta or para substituent on the aryl ring. For example, a compound having a hydrophobic aromatic halide moiety as $G_1$, i.e., a para-halophenyl is represented by General Formula 1-19:

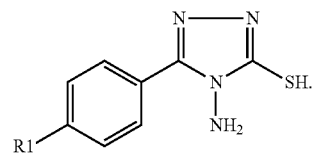

An exemplary compound having $R_1$ as a para-halogen substituent and an —SH substituent for $R_2$ is represented by Formula 1-20, and is described elsewhere herein as SD-29:

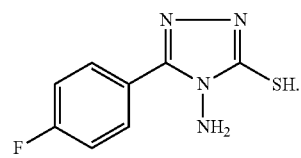

The aryl ring can be substituted with another halogen instead of fluoro, or instead of fluoro can be have a halogen-substituted lower alkyl, a halogen-substituted lower alkoxy or a halogen-substituted lower alkenyl, as indicated above.

Synthesis of the Compounds

Compounds in accordance with general formulas herein, including General Formula 1, include compounds described in WO2013/151769. The compounds can be synthesized by adapting a synthesis described in PCT/2013US/032496 (now WO2013/151769), the complete disclosure of which is incorporated herein by reference.

By way of example, a compound in accordance with formulas herein, including General Formula 1, can be prepared as shown in the following exemplary reaction scheme:

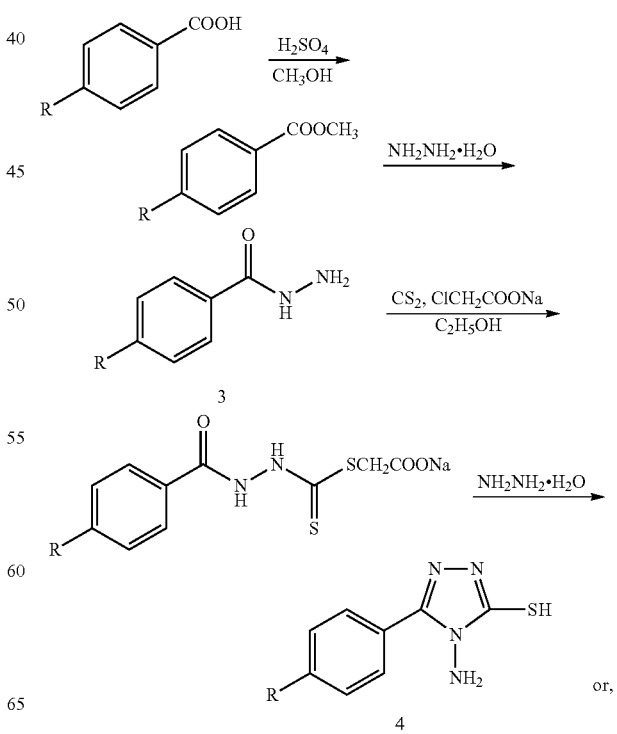

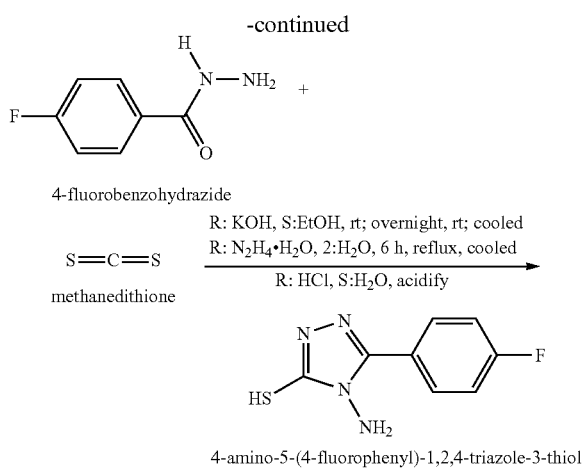

4-fluorobenzohydrazide

S═C═S
methanedithione

R: KOH, S:EtOH, rt; overnight, rt; cooled
R: N₂H₄·H₂O, 2:H₂O, 6 h, reflux, cooled
R: HCl, S:H₂O, acidify 4-amino-5-(4-fluorophenyl)-1,2,4-triazole-3-thiol Alternatively, compounds in accordance with General Formula 1 having thiol at $G_2$ can be synthesized as follows, with the synthesis being adaptable for others of such compounds as described herein. The hydrazide (0.04 mol) and KOH (0.04 mol) in 50 cm³ MeOH were treated with $CS_2$ (0.04 mol), and the mixture was stirred for 16 h at room temperature. Diethyl ether (50 cm³) was added, and the precipitated solid was filtered, washed with ether, and vacuum-dried at 78° C. in a drying pestle. The potassium salts of substituted dithiocarbazinic acids were used for □□e next step without further purification. The potassium salt of the substituted dithiocarbazinic acid (0.02 mol) and hydrazine hydrate (0.04 mol) in 2.0 cm³ water were heated under reflux with stirring for 0.5-1.5 h. The color of the reaction mixture changed to green with the evolution of hydrogen sulfide, and a homogeneous solution was formed in half an hour. When evolution of hydrogen sulfide ceased (lead acetate test), the reaction mixture was diluted with 50 cm³ cold water and acidified with 6 N hydrochloric acid. The precipitated solid was filtered, washed with cold water, and recrystallized from aqueous EtOH. 4-amino-5-(3-fluorophenyl)-2,4-dihydro-3H-1,2,4-triazole-3-thione (5e, $C_8H_7FN_4S$) Yield 72%; m.p.: 220° C.; 1H NMR ((CD3) 2CO, 300 MHz): d=5.53 (s, 2H, NH₂), 7.34 (m, 1H, Ar—H), 7.79 (m, 1H, Ar—H), 8.01-8.04 (m, 2H, Ar—H), 12.94 (s, 1H, NH) ppm; 13C NMR ((CD3)2CO, 75 MHz): d=114.7 (d, JC, F=24.7 Hz, C2-arom.), 117.2 (d, JC,F=21.0 Hz, C4-arom.), 124.0 (d JC,F=3.0 Hz, C6-arom.), 128.2 (d, JC,F=9.0 Hz, C5-arom.), 130.6 (d, JC,F=8.3 Hz, C1-arom.), 148.4 (C-5), 162.4 (d, JC, F=242.3 Hz, C3-arom.), 168.6 (C-3) ppm; IR (KBr); v1/43, 288; 3; 171; 1; 536; 1; 315; 1; 192 cmŷ1; MS (El): m/z (%)=210 (M, 100), 195 (2), 139 (25), 122 (34), 95 (23), 75 (8), 60 (12).

Compounds in accordance with the general formulas, including General Formula 1, can also be synthesized by adapting procedures described in J. Medicinal Chemistry, 52(14), 4200-4209 (2009); Condensed heterocyclic systems containing bridgehead nitrogen atom: synthesis and antimicrobial activity of s-triazolo[3, 4-b][1, 3, 4]thiadiazines, thiazolo[3, 2-b]-s-triazoles and isomeric thiazolo[2, 3-c]-s-triazoles. Indian Journal of Chemistry, Section B: Organic Chemistry Including Medicinal Chemistry (2002), 41B, (2), 403-406; and A novel 5-mercapto triazole Schiff base as a selective chromogenic chemosensor for Cu²⁺, Liu, Ming-Xia et al., Spectrochimica Acta, Part A: Molecular and Biomolecular Spectroscopy, 79(5), 1837-1842; 2011. Producing compounds wherein the "R" type substituent on the phenyl group represents another group besides halogen (fluorine in the example), or other positional isomers, can be prepared by adapting the disclosed synthesis routes. $SCH_2COOH$, amide, ═S and ═O are alternatives to —SH. Amide includes, by way of example, —N(CH₃)₂. Besides fluorine, halogen includes chlorine and bromine, although other electronegative groups, such as fluoromethoxy, difluoromethoxy, trifluoromethoxy and trifluoromethyl as examples, can substitute for a halogen.

In another aspect, compounds in accordance with the disclosure can be synthesized as shown in the following exemplary reaction scheme.

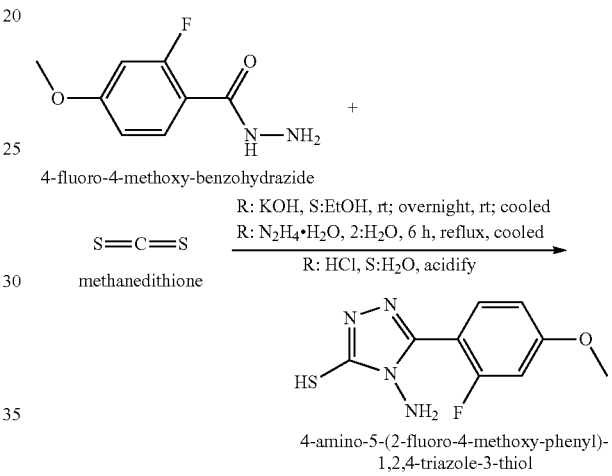

4-fluoro-4-methoxy-benzohydrazide

S═C═S
methanedithione

R: KOH, S:EtOH, rt; overnight, rt; cooled
R: N₂H₄·H₂O, 2:H₂O, 6 h, reflux, cooled
R: HCl, S:H₂O, acidify 4-amino-5-(2-fluoro-4-methoxy-phenyl)-1,2,4-triazole-3-thiol It will be appreciated compounds having different substituent(s) instead of the exemplified compound having a para-methoxy substitutent or the ortho-fluorine substitution on the phenyl ring can be synthesized by adapting an appropriate synthesis, including those described in J. Medicinal Chemistry, 52(14), 4200-4209 (2009); Condensed heterocyclic systems containing bridgehead nitrogen atom: synthesis and antimicrobial activity of s-triazolo[3, 4-b][1, 3, 4] thiadiazines, thiazolo[3, 2-b]-s-triazoles and isomeric thiazolo[2, 3-c]-s-triazoles, Indian Journal of Chemistry, Section B: Organic Chemistry Including Medicinal Chemistry (2002), 41B, (2), 403-406; and 3. A novel 5-mercapto triazole Schiff base as a selective chromogenic chemosensor for Cu2+, Liu, Ming-Xia et al., Spectrochimica Acta, Part A: Molecular and Biomolecular Spectroscopy, 79(5), 1837-1842; 2011, the complete disclosures of which are incorporated herein by reference. Thus, producing compounds wherein the "R" type substituent on the phenyl ring represents aryl or another group can be prepared. In addition to the exemplified fluorine substitution, other halogen substitution is contemplated, such as bromine and chlorine, as are other electronegative groups, such as fluoromethoxy, difluoromethoxy, trifluoromethoxy and trifluoromethyl as examples. $SCH_2COOH$, amide, ═S and ═O are alternatives to —SH. Amide includes, by way of example, —N(CH₃)₂.

Compounds in accordance with the general formulas, including General Formula 1, may also be synthesized as shown in the following illustrative reaction scheme:

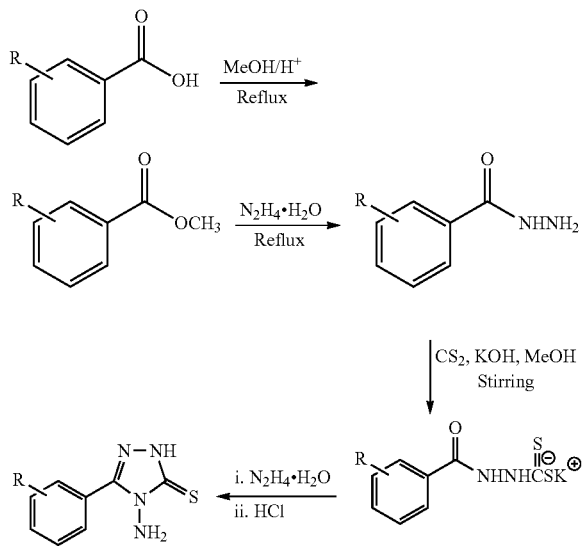

Besides fluorine substitution for R, other halogen substitutions are contemplated, such as bromine and chlorine, as well as electronegative groups, such as fluoromethoxy, difluoromethoxy, trifuoromethoxy and trifluoromethyl as examples.

Synthesis methods and the compounds are described in U.S. provisional application 62/313,421 filed Mar. 25, 2016 and in U.S. provisional application 62/374,413, filed Aug. 12, 2016, and the complete disclosures of such applications are incorporated herein by reference.

Inhibiting Expression of at Least a Portion of a Virus Genome Containing an Internal Ribosome Entry Site Compounds in accordance with General Formula 1, including derivatives in accordance with General Formulae 1-1 to 1-20, can be evaluated for the capacity to inhibit expression of at least a portion of a virus genome containing an IRES sequence by administering the compound, or a pharmaceutically acceptable salt of the compound, to a cell culture and exposing the cell culture to a viral infection. After a sufficient amount of time, the culture can be examined to determine the expression of the complete viral genome by assessing the amount of at least one protein within the viral genome. If the amount of at least one protein within the viral genome is diminished compared to that within an identical infected cell culture not treated with the compound or its salt, then the compound would be capable of inhibiting expression of at least a portion of the viral genome. By inhibiting expression of at least a portion of the viral genome, the compound, or its pharmaceutically acceptable salt, administered to the cultural would be capable of inhibiting proliferation of the virus infecting the cell culture.

The expression of a protein within the viral genome can be assessed by many means. For example, the protein may exhibit luminescence or phosphorescence as to permit the amount of expression to be determined by the amount of light given off by the culture and/or a lysate thereof. In combination or the alternative, the expression of a protein may be determined by the binding of various markers, such as antibodies, for proteins within the viral genome. Other means known to those skilled in the art of detecting the presence or absence of a protein within a viral genome following infection of cell culture may also be used. Regardless of the manner in which expression of protein within a viral genome is assessed, diminished amounts of the assessed protein in infected cultures treated with a compound in accordance with General Formula 1, including derivatives in accordance with any of General Formulae 1-1 to 1-20, or a pharmaceutically acceptable salt thereof, compared to identically infected cultures not treated with the compound or its salt evidences the capacity of the compound and/or its salt to inhibit expression of at least a portion of a virus genome containing an IRES sequence.

The expression of the protein assessed may be native, i.e. naturally occurring within the genome of the virus to be treated. In combination or the alternative, expression of a protein introduced to the viral genome may be assessed. Assessing the expression of an introduced protein may enable an assessment of viral proliferation by means not normally permitted by the native viral genome. For example, proliferation of the HIV1 virus can be assessed using luminescence with the HIV1 modified pNL4-3.Luc.R-E-virus. A plasmid map of the HIV1 modified pNL4-3.Luc.R-E-virus is shown in FIG. 1. As can be seen from the plasmid map shown in FIG. 1, the HIV1 modified pNL4-3.Luc.R-E-virus includes a firefly luciferase gene inserted into the pNL4-3 nef gene. Accordingly, proliferation of the HIV1 modified pNL4-3.Luc.R-E-virus will entail production of the luciferase protein. As the luciferase protein causes fireflies to glow, production of the luciferase protein by infected cells as a result of viral proliferation will enable infected cells actively proliferating the HIV1 modified pNL4-3.Luc.R-E-virus to glow. However, if cells infected with the HIV1 modified pNL4-3.Luc.R-E-virus do not glow when administered a compound in accordance with General Formula 1, including derivatives in accordance with General Formulae 1-1 to 1-20, or pharmaceutically acceptable salts thereof, then the compound or its salt is capable of inhibiting expression of at least a portion of the HIV1 virus genome containing an IRES sequence. Inhibiting expression of at least a portion of the HIV1 virus genome, the compound would inhibit proliferation of the HIV1 virus.

Accordingly, compounds in accordance with General Formula 1, including derivatives in accordance with General Formulae 1-1 to 1-20, or pharmaceutically acceptable salts thereof, can be assessed for the ability to inhibit proliferation of the HIV1 by infecting CEM T cells with the HIV1 modified pNL4-3.Luc.R-E-virus. Prior to infection the CEM T cells can be treated with a compound in accordance with General Formula 1, including derivatives in accordance with General Formulae 1-1 to 1-20, or pharmaceutically acceptable salts thereof. For purposes of comparison, CEM T cells not treated with such a compound and/or salt should also be infected with the HIV1 modified pNL4-3.Luc.R-E-virus.

Figure 2:
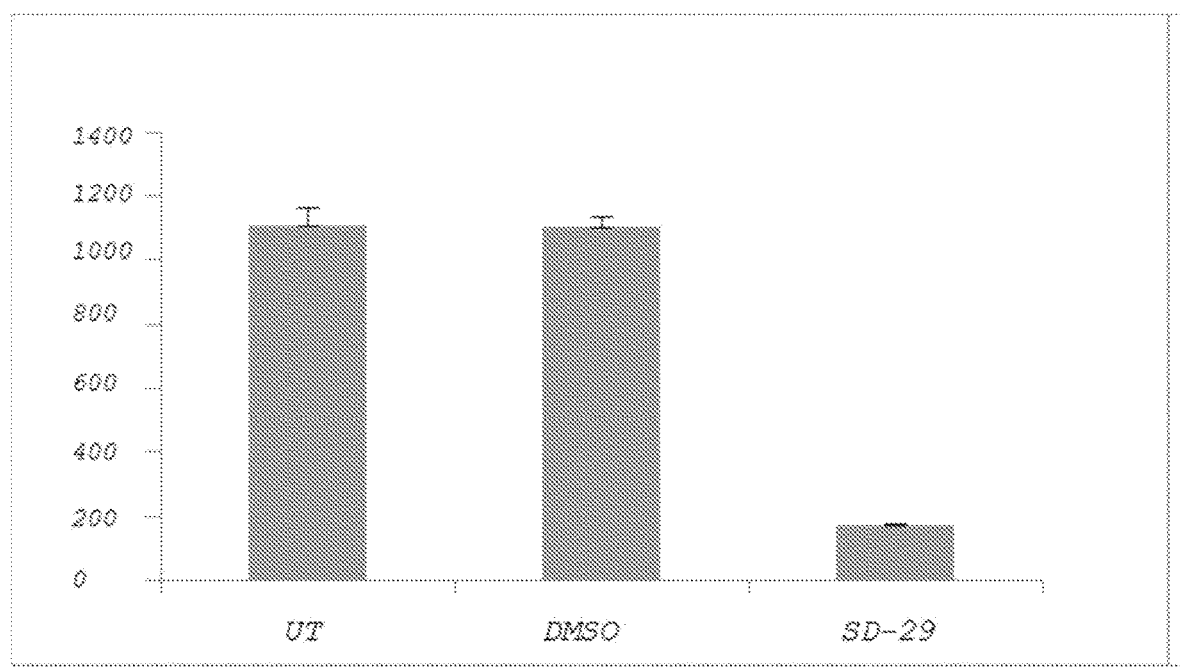
FIG. 2 shows a comparison of the luminescence observed from untreated CEM T cells, CEMT T cells pretreated with a compound capable of associating with RACK1 and blocking access to Tyr$^{248}$, and CEM T cells pretreated with DMSO after infection with the HIV1 modified pNL4-3.Luc.R-E-virus.

Shown in FIG. 2 is a comparison of the luminescence observed from untreated CEM T cells, CEMT T cells pretreated with SD-29, and CEM T cells pretreated with DMSO after infection with the HIV1 modified pNL4-3.Luc.R-E-virus. The compound SD-29, as shown by its structure below, is a derivative of a compound in accordance with General Formula 1, wherein the five member heterocyclic ring of the azole moiety comprises a nitrogen at the 1 position, a nitrogen at the 3 position, and a nitrogen at the 4 position comprising a hydrophilic moiety, a hydrophilic amine moiety is bonded to the nitrogen atom at position 1 of the heterocyclic ring of the azole moiety, $G_2$ is sulfhydryl donor/acceptor moiety, and $G_1$ is a hydrophobic aromatic halide moiety.

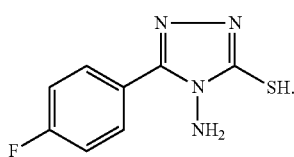

SD-29

Prior to infection with the HIV1 modified pNL4-3.Luc.R-E-virus, the CEM T cells were pretreated with either SD-29 or DMSO (100 M) or left untreated. After infection with the HIV1 modified pNL4-3.Luc.R-E-virus, the CEM T cells were cultured at $0.5 \times 10^6$ cell/mL in 6-well plates at 37° C. and 5% $CO_2$. To assess luminescence, 100 μL of the cell suspension and 100 mL of reconstituted luciferase buffer (Luclite Kit, Perkin Elmer) were added to wells and allowed to incubate for 10 minutes. After which lysates were transferred into white plates from Perkin Elmer and luminescence measured using Labsystems Luminoscan RT equipment from Perkin Elmer. A comparison of the measured luminescence is shown in FIG. 2.

As can be seen from FIG. 2, untreated CEM T cells and DMSO treated CEM T cells display significantly higher luminescence than CEM T cells treated with SD-29. Accordingly, treatment with SD-29 significantly reduced proliferation of the HIV1 modified pNL4-3.Luc.R-E-virus.

Figure 3:
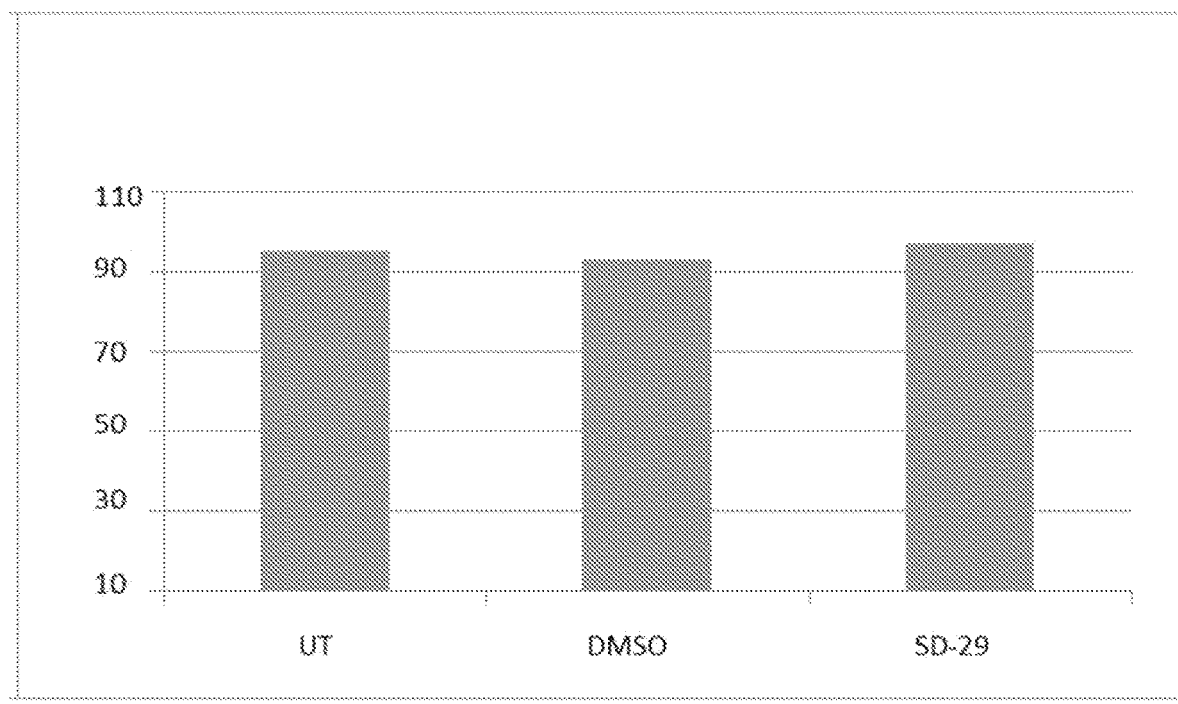
FIG. 3 shows the percent of viable untreated CEM T cells, CEMT T cells pretreated with a compound capable of associating with RACK1 and blocking access to Tyr$^{248}$, and CEM T cells pretreated with DMSO after infection with the HIV1 modified pNL4-3.Luc.R-E-virus.

It is possible that the diminished expression of a protein within the genome of a virus containing an IRES sequence may have been brought about by the compound inhibiting the ability infected cells to survive. If the compound or salt diminishes viability or is otherwise toxic to the cell, then diminished expression of a protein within the genome of a virus containing an IRES sequence may be the result of infected cells dying before sufficient levels of the protein can be expressed. Determining if diminished expression of a protein is the result of cell death or other toxic effects of the compound or salt may be accomplished by assessing the viability of cells after administration of the compound or salt. Accordingly, in some embodiments of assessing the ability of a compound in accordance with General Formula 1, including derivatives in accordance with any of General Formulae 1-1 to 1-20, or pharmaceutically acceptable salts thereof, to inhibit the expression of at least a portion of a virus genome containing an IRES sequence, the compound or salt may be assessed for its ability to preserve viability of cells following administration. FIG. 3 shows the percent of viable CEM T cells after infection. As can be seen from FIG. 3, treatment with SD-29 did not decrease viability of the infected cells, demonstrating the ability of SD-29 to reduce expression of luciferase portion of the HIV1 modified pNL4-3.Luc.R-E-virus genome containing an IRES sequence was not brought about by decreased cellular viability. Accordingly, the methods include administering a therapeutically effective amount of a compound(s) in accordance with General Formula 1, including any of General Formulae 1-1 to 1-20, or pharmaceutically acceptable salts thereof, for treating against the viral infection while preserving viability of the cells (inclusive of cells in vivo and in vitro).

It should be appreciated from FIGS. 2 and 3 that inhibition of RACK1 mediated expression of proteins within an IRES reading frames by SD-29 does not decrease cell viability. Accordingly, SD-29 induced inhibition of RACK1 that affect regulated expression of viral proteins within an IRES reading frames does not decrease host cell viability.

The ability of a compound in accordance with General Formula 1, including derivatives in accordance with General Formulae 1-1 to 1-20, or pharmaceutically acceptable salts thereof, to inhibit the expression of at least a portion of a virus genome containing an IRES sequence can be also be determined by assessing the expression of a native protein within a viral genome. In some embodiments, the ability of a compound or pharmaceutically acceptable salt to inhibit expression of native protein can be assessed by using antibodies for a protein normally expressed from the virus genome. For example, HIV p24 gag is a protein normally expressed by HIV1 that can be detected using the HIVI p24 antibody. Accordingly, compounds in accordance with General Formula 1, including derivatives in accordance with any of General Formulae 1-1 to 1-20, or pharmaceutically acceptable salts thereof, can be assessed for the ability to inhibit proliferation of the HIV1 by infecting CEM T cells with the HIV1 modified pNL4-3.Luc.R-E-virus and assessing the expression of HIV p24 gag with the HIV p24 antibody.

Figure 4:
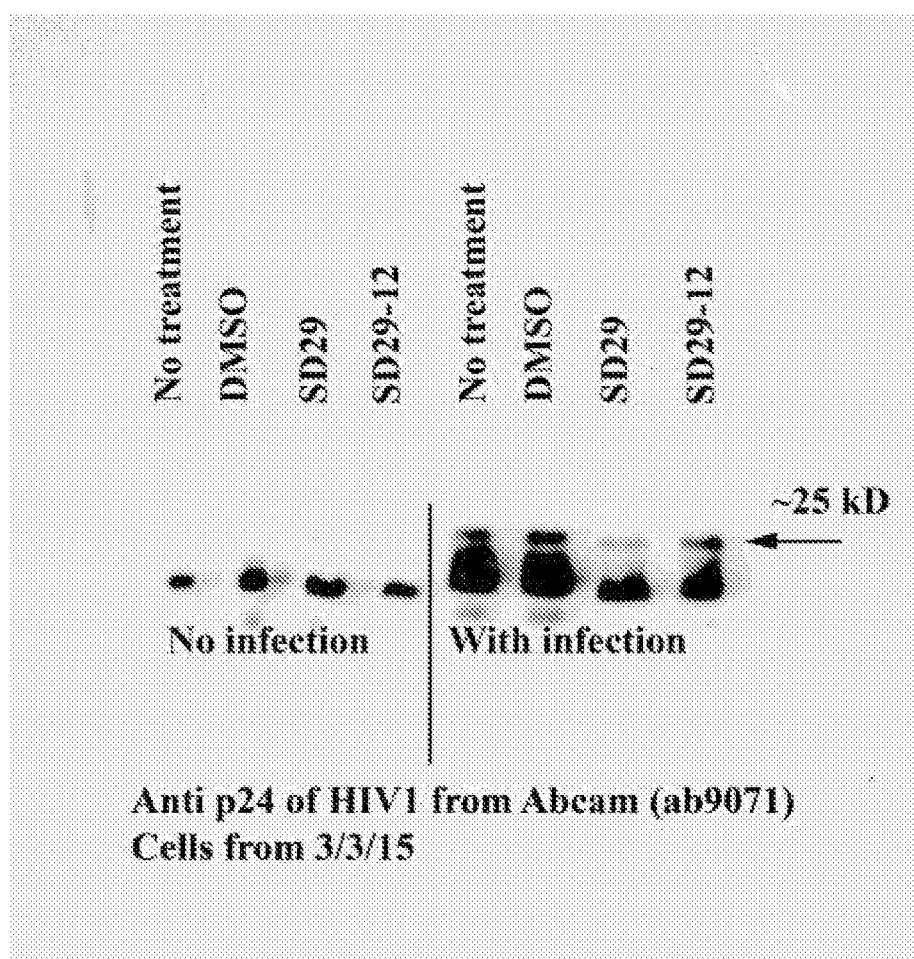
FIG. 4 shows a Western assay of lysates from CEM T cells and CEM T cells infected with the HIV1 modified pNL4-3.Luc.R-E-virus.

FIG. 4 shows a Western assay of lysates from CEM T cells and CEM T cells infected with the HIV1 modified pNL4-3.Luc.R-E-virus. The infected and uninfected CEM T cells were either not treated or treated with DMSO, SD-29 or SD-29-12. The compound SD-29-12, as shown by its structure below, is a compound comprising an triazole moiety having an amine attached to the nitrogen at position 1 of the triazole moiety, an aryl moiety attached to the carbon at position 5 of the triazole moiety, and a sulfide moiety having an electron withdrawing group attached to the carbon at position 2 of the triazole moiety.

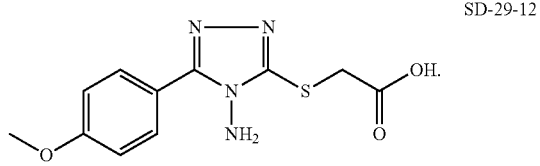 [SMILES: COc1ccc(-c2nnc(SCC(=O)O)n2N)cc1]

SD-29-12

The isolated electron withdrawing group within the sulfide moiety may weaken hydrogen bonds between the sulfur of the sulfide moiety and $Ser^{244}$ and/or $Trp^{249}$ or RACK1. The weakened hydrogen bonds may prevent SD-29-12 from remaining attached to RACK1 at sufficient levels to fully prevent the HIV1 modified pNL4-3.Luc.R-E-virus from proliferating by using IRES sequences within its genome to hijack ribosomes deactivated by eIF-6. As shown in FIG. 4, treatment with SD-29-12 does not inhibit expression of HIV p24 gag in cells infected with the HIV1 modified pNL4-3.Luc.R-E-virus. In contrast, the reduced intensity of the p24 gag band at 24 kD shows that SD-29 does inhibit expression of the portion of the HIV1 modified pNL4-3.Luc.R-E-virus genome corresponding to HIV p24 gag. Accordingly, compounds in accordance with General Formula 1, including derivatives in accordance with any of General Formulae 1-1 to 1-20, or pharmaceutically acceptable salts thereof, can be assessed for the ability to inhibit proliferation of the HIV1 virus by utilizing a Western assay and the HIV p24 antibody to assess the expression of HIV p24 gag, and a present method includes the administration of at least one such assessed compound having the ability to inhibit proliferation of the HIV1 virus by utilizing a Western assay and the HIV p24 antibody to assess the expression of HIV p24 gag.

Figure 5:
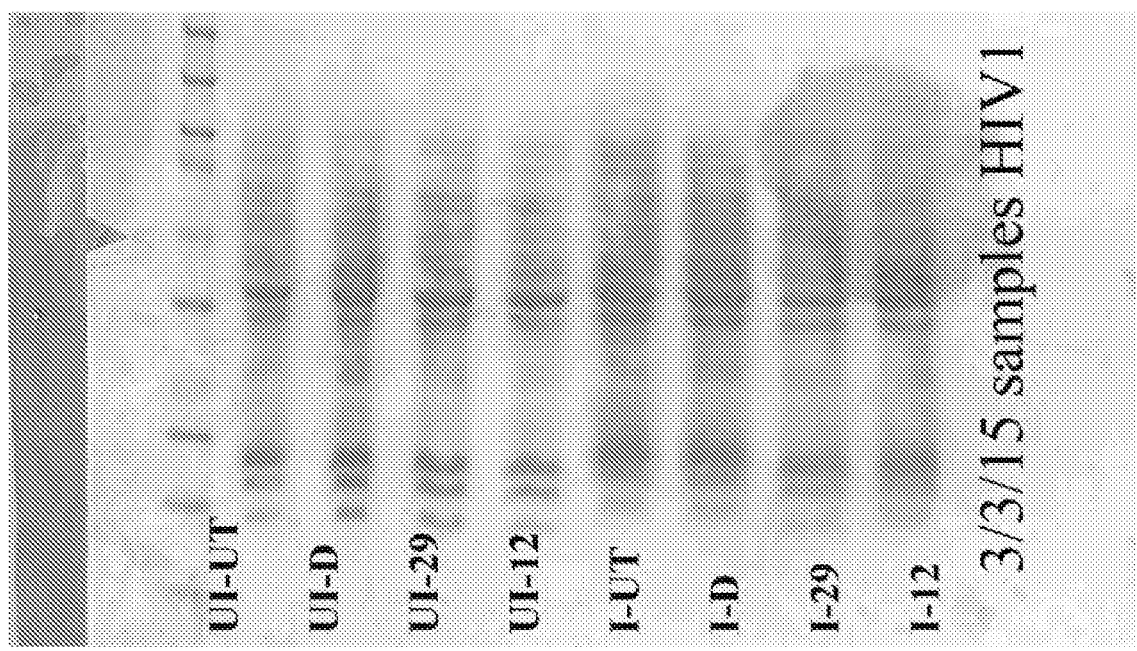
FIG. 5 shows ponceau staining for the Western assay shown in FIG. 4.

A compound or salt may be wrongly classified as capable of inhibiting expression of at least a portion of a virus genome containing an IRES sequence due to unequal loading of proteins within an assay. In many assays, such as Western assays, the amount of staining observed is dependent upon the amount of protein present. It is possible, however, that a cell culture administered a compound or salt may experience diminished expression of several proteins, and not just proteins within the genome of a virus infecting the culture. In such a situation, the lysates from the culture administered a compound or salt would have less proteins than lysates from a culture not administered the compound or salt. This would result in an unequal loading of proteins within each lane of the assay. Accordingly, some embodiments of assessing the ability of a compound in accordance with General Formula 1, including derivatives in accordance with any of General Formulae 1-1 to 1-20, or pharmaceutically acceptable salts thereof, to inhibit the expression of at least a portion of a virus genome containing an IRES sequence may include assessing the amount of protein provided in each lane of the Western assay. In some embodiments, equivalent protein loading can be assessed by ponceau staining. FIG. 5 shows ponceau staining for the previously described Western assay. As can be seen from FIG. 5, almost equal amounts of protein were loaded in each lane. A present method includes the administration of at least one such compound assessed as inhibiting the expression of at least a portion of virus genome containing an IRES sequence.

Inhibition of Triggered Expression of at Least a Portion of a Virus Genome Containing an Internal Ribosome Entry Site Some viruses, such as the HSV-1 virus, contain an IRES sequence within a portion of their genome that triggers the production of other portions of the viral genome. When mRNA corresponding to this triggering portion of the genome reaches the ribosomes of the infected cell, it triggers the production of protein that stimulates the production of other portions of the viral genome. For instance, the HSV-1 virus contains immediate-early (IE) genes that include ICP0, -4, -22, -27, and -47 . These genes are expressed shortly after entry of the virus into the infected cell. The viral proteins produced by the expression of IE genes triggers the expression of delayed-early (DE) genes. These genes regulate the replication of the HSV-1 viral genome. That is, the DE genes make more genetic copies of the HSV-1 virus. The final genes expressed, the late (L) genes, create proteins constructing the viron into which genetic copies of the HSV-1 virus are packaged to be sent out to infect other cells.

Compounds in accordance with General Formula 1, including derivatives in accordance with any of General Formulae 1-1 to 1-20, can be evaluated for the capacity to inhibit triggered expression of at least a portion of a virus genome containing an IRES sequence by administering the compound, or a pharmaceutically acceptable salt of the compound, to a cell culture and exposing the cell culture to a HSV-1 infection. After a sufficient amount of time, the culture can be examined to determine the expression of IE, DE and L genes. If the amount of at least one protein corresponding to an IE gene and at least one protein corresponding to a DE and/or L gene within the viral genome is diminished compared to that within an identical infected cell culture not treated with the compound or its salt, then the compound would be capable of inhibiting triggered expression of at least a portion of the viral genome. By inhibiting triggered expression of at least a portion of the viral genome, administering the compound, or its pharmaceutically acceptable salt, to the culture would be capable of inhibiting proliferation of the virus infecting the cell culture.

Compounds in accordance with General Formula 1, including derivatives in accordance with any of General Formulae 1-1 to 1-20, or pharmaceutically acceptable salts thereof, can be assessed for the ability to inhibit triggered expression of at least a portion of the HSV-1 genome by infecting Hep-2 cells with the HSV-1 virus. Prior to infection the Hep-2 cells can be treated with a compound in accordance with General Formula 1, including derivatives in accordance with any of General Formulae 1-1 to 1-20, or pharmaceutically acceptable salts thereof. For purposes of comparison, Hep-2 cells not treated with such a compound and/or salt should also be infected with the HSV-1 virus.

Figure 6:
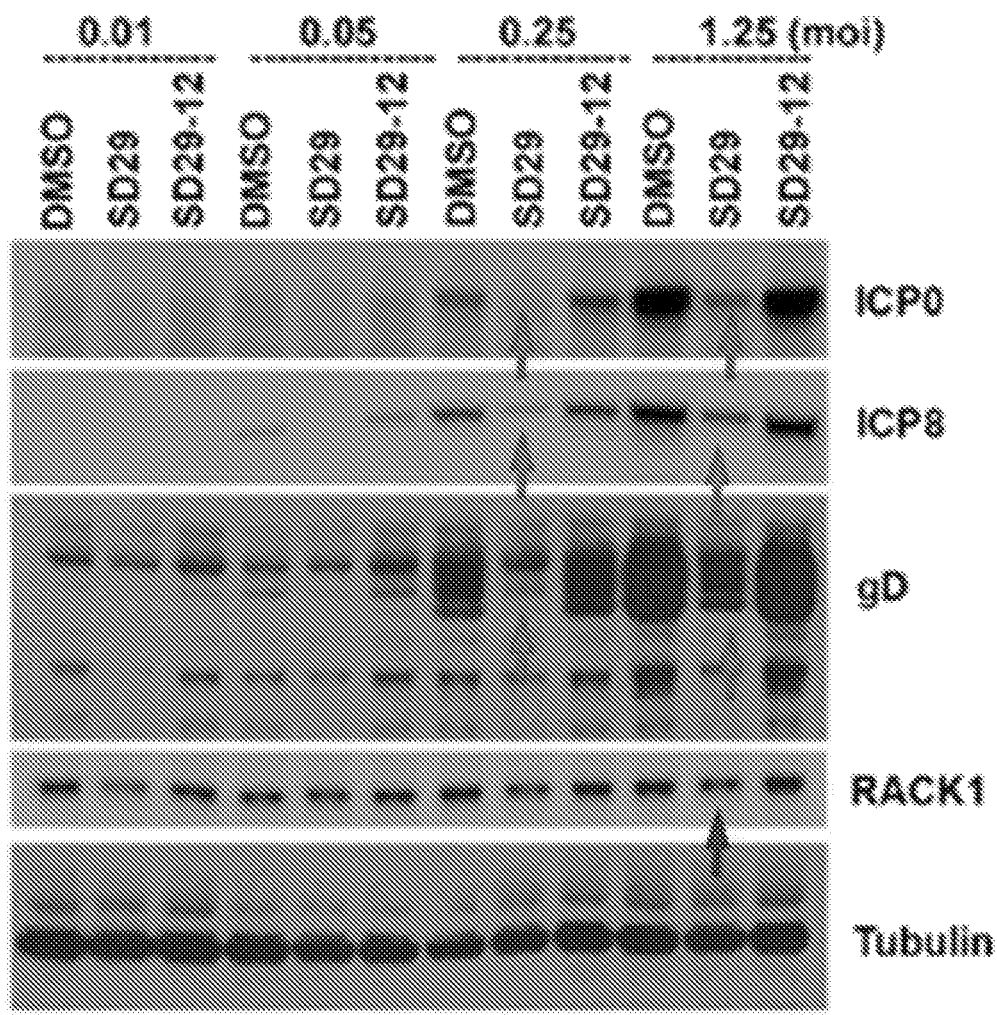
FIG. 6 shows a Western Assay showing expression of RACK-1, the IE protein ICP0, DE protein ICP8 and the L protein gD following infection of Hep-2 cells at varying multiplicity of infection (MOI) of HSV-1.

FIG. 6 is a Western assay showing expression of RACK-1, the IE protein ICP0, DE protein ICP8 and the L protein gD following infection of Hep-2 cells at varying multiplicity of infection (MOI) of HSV-1. In FIG. 6, ICP0 designates immediate early viral protein, ICP8 designates early viral protein, and dD designates late viral protein. Tubulin was used as a sample loading control. Prior to infection, Hep-2 cells were treated with DSMO as a control, 100 µM SD-29 or 100 µM SD29-12. After 24 hours of pretreatment, the Hep-2 cells were infected with HSV-1 at either 0.01, 0.05, 0.25 or 1.25 MOI (from 0.01 to 1.25). Twenty hours after infection, whole cell lysate samples were obtained and the Western assay shown in FIG. 6 was performed to examine protein levels.

As shown in FIG. 6, treatment with SD-29 reduced expression of RACK-1 and the expression of IE, DE and L HSV-1 proteins. All the key proteins needed by HSV-1 virus replication were repressed. Accordingly, treatment with SD-29 significantly inhibited triggered expression of at least a portion of the HSV-1 genome. The demonstrated inhibited triggered expression of at least a portion of the HSV-1 genome supports efficacy for compounds in accordance with General Formula 1, including derivatives in accordance with any of General Formulae 1-1 to 1-20, for inhibiting the ability of viruses to infect cells, and thus demonstrating efficacy for repressing a key protein(s) required for viral replication of a virus utilizing IRES based replication, such as HSV-1 viral replication.

The ability of a virus to infect cells can be assessed using a plaque assay. In a plaque assay, an infected cell culture is grown under a nutrient gel. During culturing, the virus being study infects cells and replicates. However, the spread of virus to other cells is limited by the overlaying nutrient gel. As such, replicated virus released from one infected cell can only infect neighboring cells. The spread of virus amongst neighboring cells creates a plaque that can be visualized by staining. By counting the visible plaques, the amount of plaque forming units (pfu) per mL can be determined. If cells treated with a compound display a reduced amount of pfu compared to cells not treated with the compound after being infected with same amount of viral particles, then the reduction in pfu would have to be result of the ability of the compound to inhibit proliferation of the compound to inhibit proliferation of the virus. Thus, the ability of a compound in accordance with General Formula 1, including derivatives in accordance with any of General Formulae 1-1 to 1-20, to inhibit the ability of HSV-1 to proliferate can be assessed with a plaque assay.

The results of such a plaque assay are shown in Table 1. Hep-2 cell monolayers were placed in well plates. The plated Hep-2 cells were treated with either DSMO as a control, 100 µM SD-29 or 100 µM SD29-12. A total of 6 well plates were prepared for each treatment condition. To each treated well plate an HSV-1 infecting solution comprising 1 mL of supernatants containing of the same amount of serially diluted HSV-1 particles were added. Accordingly, the treated well plates were infected with infection solutions containing the same amount of HSV-1 particles. After adsorption for 2 hours, the medium was removed and the treated cells were washed twice with serum-free DMEM and overlaid with phenol-free DMEM containing 5% FCS, 0.5% low-melting point agarose (GIBCO), and 1% penicillin-streptomycin. After either 0, 6, 12, 24 hours, the plaques present in each treated well plate were stained red and the number of plaques presented counted. Table 1 reports the mean plaque forming unit (pfu) determined for each treated well plate after averaging the number of pfu from the different plates receiving the same treatment. A graphical representation of the data presented in Table 1 is shown in FIG. 7.

Figure 7:
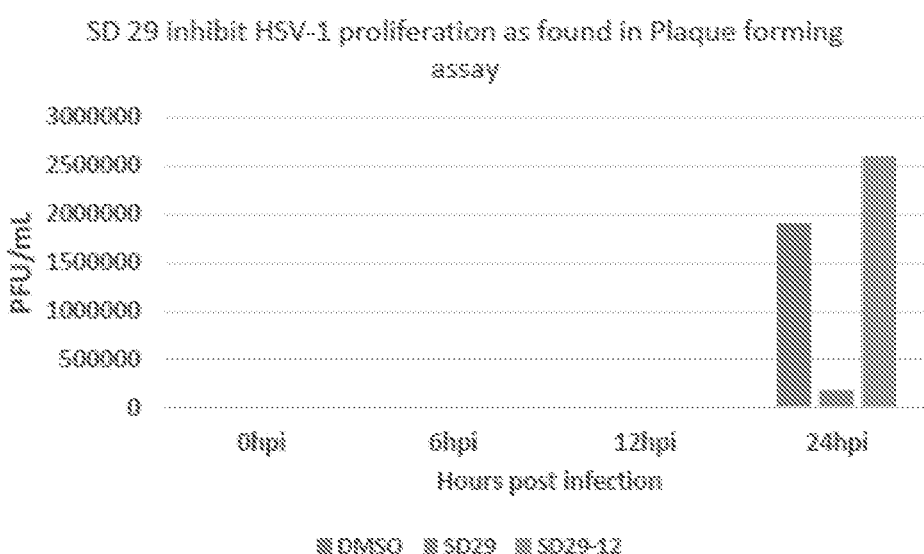
FIG. 7 shows the mean plaque forming units determined for plated Hep-2 cells treat with either DSMO as a control, 100 µM SD-29 or 100 µM SD29-12 at various times following infection.

As can be seen from Table 1 and FIG. 7, SD-29 treated well plates showed a reduced number of pfu compared to control treatment with DMSO. Since the Hep-2 cells in the SD-29 treated and DMSO treated well plates were each infected with infecting solutions containing the same amount of HSV-1 viral particles, the reduced pfu of the SD-29 treated well plates shows that treatment with SD-29 inhibits the ability of HSV-1 to proliferate. The inhibited proliferation of HSV-1 indicates a compound(s) in accordance with General Formula 1, including derivatives in accordance with any of General Formulae 1-1 to 1-20, can inhibit the ability of viruses to infect cells.

TABLE I

Plaque forming Assay

|  | DMSO | SD29 | SD29-12 |
| --- | --- | --- | --- |
| 0 hpi | 0 | 0 | 0 |
| 6 hpi | 320 | 0 | 380 |
| 12 hpi | 2600 | 100 | 3600 |
| 24 hpi | 1900000 | 180000 | 2600000 |

Figure 8:
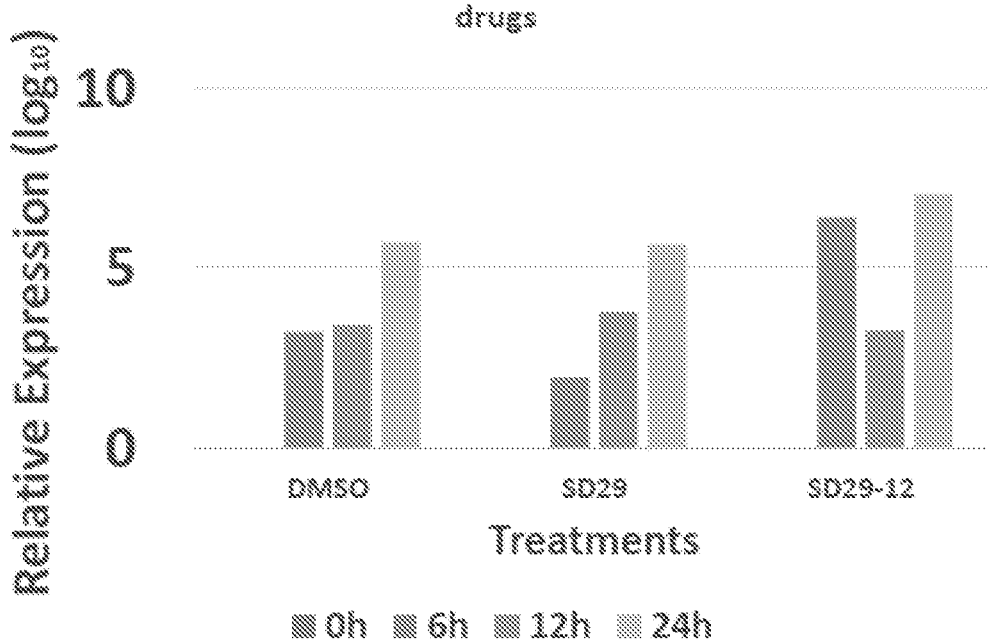
FIG. 8 shows the amount of mRNA of the IE gene ICP-0 detected in Hep-2 cells treated with either DSMO as a control, 100 µM SD-29 or 100 µM SD29-12 at various times following infection with HSV-1.

The inhibition of triggered expression of at least a portion of the HSV-1 genome and the inhibited proliferation of HSV-1, which may be the result of the former, indicate that compounds in accordance with General Formula 1, including derivatives in accordance with any of General Formulae 1-1 to 1-20, can treat viral infections. The treatment provided by compounds in accordance with General Formula 1, including derivatives in accordance with any of General Formulae 1-1 to 1-20, may be the result of either inhibition of transcription of viral mRNAs containing an IRES or the inhibited expression of viral proteins encoded by such within the IRES reading frame of such an mRNA. Determining whether mRNA transcription or protein expression is being inhibited can be accomplished by assessing the amount of mRNA containing an IRES is diminished by treatment with a compound in accordance with General Formula 1, including derivatives in accordance with any of General Formulae 1-1 to 1-20. FIG. 8 reports the amount of mRNA of the IE gene ICP-0 detected in Hep-2 cells following treatment with SD-29.

Hep-2 cells were pretreated with either DSMO as a control, 100 µM SD-29 or 100 µM SD29-12. After 24 hours of pretreatment, the Hep-2 cells were infected with HSV-1. At 0, 6, 12 and 24 hours after infection, the total RNA within the cells was isolated. Utilizing the Invitrogen Two Step qPCR kit, cDNA was synthesized from the RNA. Synthesized cDNA corresponding to the IE gene ICP-0 was then amplified using a Bio-Rad's CFX qPCR machine. Actin cDNA was also amplified as a control. Delta-delta Ct values were used to calculate the fold difference in expression of ICP-0 mRNA.

As shown in FIG. 8, Hep-2 cells treated with DMSO and SD-29 showed similar levels of ICP-0 mRNA at 0, 6, 12, and 24 hours after infection with HSV-1. The similar ICP-0 mRNA expression in DMSO and SD-29 treated cells indicates that treatment with SD-29 does not inhibit transcription of mRNA corresponding to IE genes. The lack of inhibited transcription of mRNA corresponding to viral IE genes indicates that the inhibition of triggered expression of at least a portion of the HSV-1 genome and the inhibited proliferation of HSV-1 induced by compounds in accordance with General Formula 1, including derivatives in accordance with General Formulae 1-1 to 1-20, is the result of the inhibited expression of viral proteins encoded within an IRES reading frame. Thus, the treatment provided by compounds in accordance with General Formula 1, including derivatives in accordance with any of General Formulae 1-1 to 1-20, results, at least in part, from the inhibited expression of viral proteins encoded within IRES reading frames.

A method of treatment as described herein involves inducing inhibition of RACK1 to affect (inhibit) the regulated expression of viral proteins within an IRES reading frame (viruses utilizing IRES based replication), by administering a compound as described, such as General Formulae 1 (e.g., General Formula 1-18 and, to mention a SD-29 as a compound by way of an example), to a patient or cells. This inducing inhibition of RACK1 is applicable to animal and human viruses utilizing IRES based replication, and includes viruses from the Flaviviridae, Picornaviridae, Herpesviridae, Retroviridae, and Dicistroviridae families, by way of example. Such viruses include, for example, HIV (e.g., HIV-1 and HIV-2), herpes simplex virus (HSV, e.g., HSV-1 and HSV-2), hepatitis (e.g. HAV, GBV-A, GBV-B, GBV-C, and HCV), polio, among others. These and other viruses utilizing IRES based replication amenable to treatment by a present method are identified in Mokrejs et al., Nucleic Acids, 2006 Jan. 1:34 (data base issue):D125-30 and Mokrejs et al., Nucleic Acids Re, January 2010, 38 (database issue):D131-136. Inhibition of the RACK1 inhibits proliferation of such viruses that utilize host ribosomal RACK1 protein in translation of IRES-containing mRNA translation.

As demonstrated, a method involving inhibiting host RACK1 can achieve an effective anti-viral treatment for the above-discussed viruses. As long as the RACK1 protein function is inhibited, the virus cannot use the host RACK1 to preferentially translate viral mRNAs using IRES. Without a functional host RACK1, the virus cannot down-regulate host mRNA translation and cannot up-regulate viral mRNA translation. The methods described herein can also be characterized as disrupting or blocking the host RACK1 function in a way that modulates the function of RACK1 to prevent/inhibit/suppress viral replication. In short, a present method that achieves inhibition of host RACK1 function by administering at least one compound within those represented by any of the general formulae including General Formula 1, clearly inhibits viral proliferation.

Although the clinical symptoms of HSV-caused diseases can be controlled with antiviral drugs (acyclovir and valacyclovir), these drugs are not strong enough to stop subclinical transmission. In addition, resistances to acyclovir and valacyclovir frequently occur. No prophylactic or therapeutic vaccine against HSV is available. Therefore, more effective preventive and/or therapeutic drugs against the HSV infection are needed. Thus, there is a need for the present methods for treating against viruses utilizing IRES based replication because, for instance, viral resistance, such as with HSV viruses, to other pharmaceutically-based treatments has been observed.

A compound or a mixture of compounds in accordance with General Formula 1, including derivatives in accordance with any of General Formulae 1-1 to 1-20, or pharmaceutically acceptable salts thereof, can be administered to a patient by various means including orally, topically, sublingually, via inhalation, and by injection. The route of administration utilized may be dependent upon numerous factors including, but not limited to, location of infection to be treated, bioavailability, sensitivity to first pass metabolism, and/or resistance to stomach acid. For example, if the infection to be treated is confined to specific location of the patient's body, then a topical administration may be appropriate. Topical application includes, for example, therapeutic patches. Likewise, if the infection to be treated is confined to lungs, then inhalation may be an appropriate route of administration. If the infection to be treated is within the blood stream, then an injection may be an appropriate route of administration. A systemic and/or local infection can also be treated by oral administration.

The infection to be treated may be a present at the time of administering a compound in accordance with General Formula 1, including derivatives in accordance with any of General Formulae 1-1 to 1-20, or pharmaceutically acceptable salts thereof, in which case the patient is one who is in need of treatment.

In combination or as an alternative, the infection to be treated may not be presented at the time of administering a compound in accordance with General Formula 1, including derivatives in accordance with any of General Formulae 1-1 to 1-20, or pharmaceutically acceptable salts thereof. For instance, the infection to be treated may be an infection a patient is at risk of developing. Treating against the infection would be prophylactic.

In any aspects of a present method, a compound in accordance with General Formula 1, including derivatives in accordance with any of General Formulae 1-1 to 1-20, or pharmaceutically acceptable salts thereof, can be administered to a cell culture, cells in vitro or in vivo, tissue sample or organ by incorporating (administering) the compound or salt into a medium comprising the tissue, organ or cell culture.

In any aspect of the methods described herein, a compound or a combination of compounds represented by General Formula 1, including derivatives in accordance with any of General Formulae 1-1 to 1-20, can be administered.

The foregoing descriptions are not intended to represent the only forms of the compounds and methods described. The percentages provided herein are by weight unless stated otherwise. Changes in form and in proportion of parts, as well as the substitution of equivalents, are contemplated as circumstances may suggest or render expedient. Similarly, while compounds and methods have been described herein in conjunction with specific embodiments, many alternatives, modifications, and variations will be apparent to those skilled in the art in light of the foregoing description.

What is claimed is:

1. A method of treating a viral infection by inhibiting expression of at least a portion of a virus genome containing an internal ribosomal entry site, said method comprising:
   a. administering a therapeutically effective amount of a compound to inhibit expression of at least a portion of a virus genome containing an internal ribosomal entry site, or a pharmaceutically acceptable salt thereof, wherein said compound is at least one compound selected from any of Formulae 1-1 through 1-20:

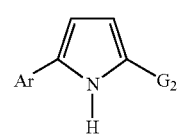

Formula 1-1

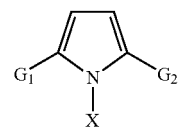

Formula 1-2

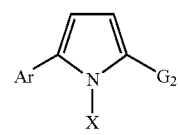

Formula 1-3

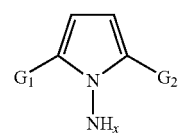

Formula 1-4

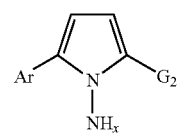

Formula 1-5

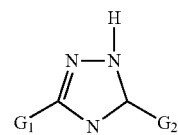

Formula 1-6

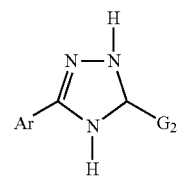

Formula 1-7

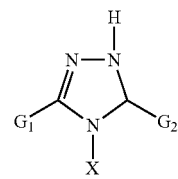

Formula 1-8

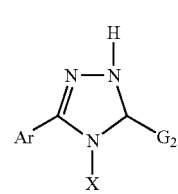

Formula 1-9

-continued

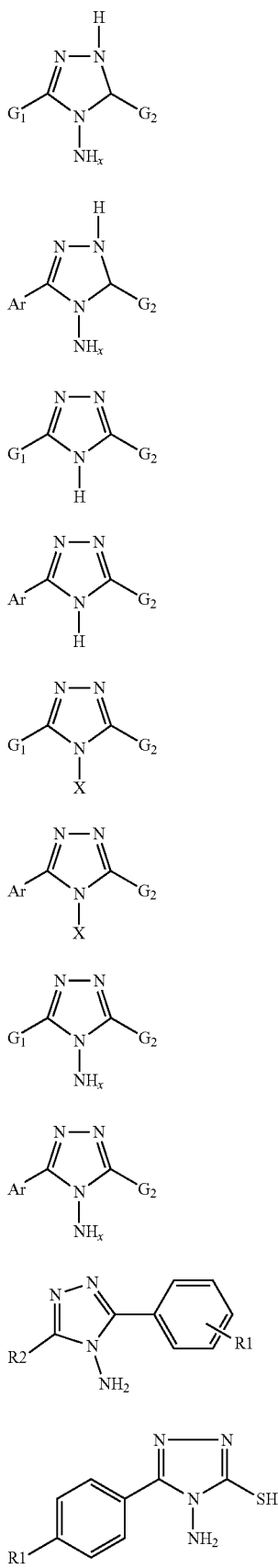

Formula 1-10
Formula 1-11
Formula 1-12
Formula 1-13
Formula 1-14
Formula 1-15
Formula 1-16
Formula 1-17
Formula 1-18
Formula 1-19

Formula 1-20 wherein $G_1$ is an aryl moiety,
wherein $G_2$ is a donor/acceptor moiety selected from the group consisting of (a)-(d):
(a) an amine moiety, an amide moiety, a thione moiety, a sulfide moiety, a sulfhydryl moiety, —C(OH)CF$_3$, —CH$_2$CH(NH$_2$)COOH, —C(O, CF$_3$)COOCH$_2$CH$_3$, —COCF$_3$, or a thioether moiety;
(b) a donor/acceptor moiety composed of: a thioether moiety, an electron withdrawing group adjacent the thioether moiety, and adjacent the electron withdrawing group, one of an electron donating group and a second electron withdrawing group adjacent the electron;
(c) a donor/acceptor moiety composed of: a thioether moiety, an electron withdrawing group adjacent the thioether moiety, an electron donating group adjacent the electron withdrawing group, and a stabilizing moiety; and
(d) —CH$_2$CONHR, —SCH$_2$COR, or —SCH$_2$ R, wherein R is a hydrogen, a hydroxyl, an aryl moiety, an aryl halide moiety, an alkyl moiety, an alkyl halide moiety, a hydrazine moiety, or a diphenyl ether moiety,
wherein X is an amine,
wherein x is 1 or 2,
wherein R1 is a halogen, a halogen-substituted lower alkyl, a halogen-substituted lower alkoxy or a halogen-substituted lower alkenyl, and
wherein R2 is —SH.

2. The method according to claim 1, wherein the donor/acceptor moiety is an amine moiety, an amide moiety, a thione moiety, a sulfide moiety, a sulfhydryl moiety, —C(OH)CF$_3$, —CH$_2$CH(NH$_2$)COOH, —C(O , CF$_3$)COOCH$_2$CH$_3$, or —COCF$_3$.

3. The method according to claim 1, wherein the donor/acceptor moiety is a thioether moiety.

4. The method according to claim 1, wherein the donor/acceptor moiety is composed of:
a thioether moiety;
an electron withdrawing group adjacent the thioether moiety; and
adjacent the electron withdrawing group one of an electron donating group and a second electron withdrawing group adjacent the electron.

5. The method according to claim 1, wherein the donor/acceptor moiety is composed of:
a thioether moiety;
an electron withdrawing group adjacent the thioether moiety;
an electron donating group adjacent the electron withdrawing group; and a stabilizing moiety.

6. The method according to claim 1, wherein the donor/acceptor moiety is —CH$_2$CONHR, —SCH$_2$COR, or —SCH$_2$ R, wherein R is a hydrogen, a hydroxyl, an aryl moiety, an aryl halide moiety, an alkyl moiety, an alkyl halide moiety, a hydrazine moiety, or a diphenyl ether moiety.

7. The method according to claim 1, wherein $G_1$ is an aryl moiety selected from the group consisting of an aromatic ether moiety, an aromatic halide moiety, and an aromatic alcohol moiety.

8. The method according to claim 1, wherein the compound is a compound of Formula 1-18, or a pharmaceutically acceptable salt thereof.

9. The method according to claim 8, wherein R1 is a halogen.

10. The method according to claim 9, wherein R1 is at the para-position.

11. The method according to claim 1, wherein the compound administered is one having been assessed for inhibiting expression of at least a portion of a virus genome containing an internal ribosomal entry site.

12. The method according to claim 1, wherein the compound administered is one having been assessed by at least one of (a) as inhibiting the proliferation of HIV1 virus as determined by utilizing a Western assay and the HIV p24 antibody to assess the expression of HIV p24 gag; or (b) by administering the compound or a pharmaceutically acceptable salt thereof to cells infected with HIV1 modified pNL4-3.Luc-E-virus whereby no glow is produced.

* * * * *